(12) United States Patent
Yamakado et al.

(10) Patent No.: US 7,790,879 B2
(45) Date of Patent: *Sep. 7, 2010

(54) ORGANIC CRYSTAL

(75) Inventors: Hideo Yamakado, Wakayama (JP); Toshiyuki Kunikiyo, Kanagawa (JP); Akito Ugawa, Kanagawa (JP)

(73) Assignee: Sony Corporation, Tokyo (JP)

( * ) Notice: Subject to any disclaimer, the term of this patent is extended or adjusted under 35 U.S.C. 154(b) by 1485 days.

This patent is subject to a terminal disclaimer.

(21) Appl. No.: 11/152,708

(22) Filed: Jun. 14, 2005

(65) Prior Publication Data

US 2006/0047111 A1    Mar. 2, 2006

Related U.S. Application Data

(62) Division of application No. 10/930,293, filed on Aug. 31, 2004, now Pat. No. 7,199,237.

(51) Int. Cl.
*C07B 47/00* (2006.01)
*C07D 487/22* (2006.01)

(52) U.S. Cl. .................................................... 540/145

(58) Field of Classification Search ............... 540/122, 540/123, 139, 145
See application file for complete search history.

(56) References Cited

U.S. PATENT DOCUMENTS 5,358,813 A    10/1994    Iijima et al.
7,199,237 B2 *  4/2007    Yamakado et al. ........... 540/122

FOREIGN PATENT DOCUMENTS

JP    2003-119255    4/2003
JP    2004-006750    1/2004

* cited by examiner

*Primary Examiner*—James O. Wilson
*Assistant Examiner*—Paul V. Ward
(74) *Attorney, Agent, or Firm*—Frommer Lawrence & Haug LLP; William S. Frommer (57) ABSTRACT

A flexible organic single crystal has a plurality of columns. The plurality of columns includes a plurality of planar organic compounds arranged so that molecular planes of molecules are respectively parallel to each other. As the organic compound, an organic compound is used that has a large molecular plane and a large area overlapping on an adjacent organic compound due to an intermolecular interaction. Further, energy changes in proportion to a strain. In this structure, when force along the direction of a stack axis is exerted, an angle formed by the stack axis and the normal of the molecular plane of the organic compound changes. Thus, the single crystal obtains flexibility.

1 Claim, 11 Drawing Sheets

ORGANIC CRYSTAL

This is a divisional of U.S. application Ser. No. 10/930,293, filed Aug. 31, 2004, the entirety of which is incorporated herein by reference.

BACKGROUND OF THE INVENTION

1. Field of the Invention

The present invention relates to a flexible organic crystal that is not broken, because the crystal is deformed in accordance with exerted force when the force such as bending force is externally exerted, and more particularly to an organic crystal used as a channel material of a flexible electronic device.

2. Description of the Related Art

A flexible electronic device such as a flexible organic field effect transistor (FET: Field Effect Transistor) has been progressively developed by using the flexibility of an organic material.

The flexible electronic device is deformed in accordance with exerted force when the force such as the bending force is externally exerted. Accordingly, since an electronic equipment in which the flexible electronic device is incorporated can be folded and carried, the electronic equipment is advantageously easily portable and hardly broken even when the force is exerted thereon. (see Japanese Patent Application Laid-Open No. 2003-119255).

There is a large difference in work function between the organic material and an inorganic material. Thus, when the transistor is formed, if the organic material is used for a channel layer and the inorganic material is used for an electrode material, a barrier is liable to be generated between the organic material and the inorganic material so that a carrier is hardly moved. Accordingly, when the flexible transistor is manufactured, the organic material is preferably used for a wiring material to make the carrier movable so that the barrier is decreased between the electrode and the channel.

Further, the channel layer is ordinarily formed with a polycrystalline organic material having a high flexibility and an electric conductivity. The channel layer formed with the polycrystalline organic material has the mobility of the carrier of about 1 cm²/Vs which is not satisfactory speed. As a cause that the mobility of the carrier is low, the generation of the diffusion of the carrier on a crystal interface is considered. As a method for suppressing the diffusion of the carrier generated on the crystal interface to improve the mobility of the carrier, a method for forming the channel layer with a single crystal organic material is exemplified.

However, the single crystal organic material is ordinarily low in its flexibility and brittle for a deformation. Accordingly, since a transistor having the channel layer formed with the single crystal organic material is not deformed in accordance with exerted formed when the force is externally exerted, the transistor is hardly used as a flexible transistor.

SUMMARY OF THE INVENTION

The present invention is proposed by taking the above-described usual problems into consideration and it is an object of the present invention to provide an organic crystal that is easily deformed in accordance with exerted force when the force is externally exerted and is high in its electric conductivity.

An organic crystal according to the present invention has columns. The columns comprise a plurality of planar organic compounds arranged so that molecular planes are respectively parallel to each other. A major axis of each of the columns is arranged along the direction of a first crystallographic axis. An interaction generated between the adjacent organic compounds in the column is stronger than an interaction between the columns. When a force along the direction of the first crystallographic axis is exerted, an angle formed by a normal of the molecular plane of each organic compound and the first crystallographic axis is equally changed in accordance with the exerted force.

The organic crystal according to the present invention has the plurality of columns. Each of the column has a structure that a plurality of planar organic compounds are arranged so that the molecular planes of molecules are respectively mutually parallel. The columns are arranged so that their longitudinal directions respectively correspond to the direction of the first crystallographic axis.

Therefore, although the organic crystal according to the present invention is a single crystal in which the organic compounds are regularly arranged, when the force in the direction of the first crystallographic axis is exerted, an angle formed by the normal of the molecular planes of the organic compounds forming each column and the first crystallographic axis is equally changed. Since the angle formed by the normal of the organic compounds forming each column and the first crystallographic axis is equally changed the organic crystal according to the present invention obtains flexibility and can be used as a material of a flexible electronic device.

BRIEF DESCRIPTION OF THE DRAWINGS

FIGS. 1A and 1B are schematic views showing an organic single crystal to which the present invention is applied. FIG. 1A shows a state that force is not exerted on the organic single crystal and FIG. 1B shows a state that the force is exerted on the organic single crystal.

FIG. 2A shows a state that force is not exerted on the organic single crystal and FIGS. 2B and 2C show states that the force is exerted on the organic single crystal.

DETAILED DESCRIPTION OF THE PREFERRED EMBODIMENTS

Now, a best mode for carrying out the present invention will be described below in detail by referring to the drawings.

Figure 1A:
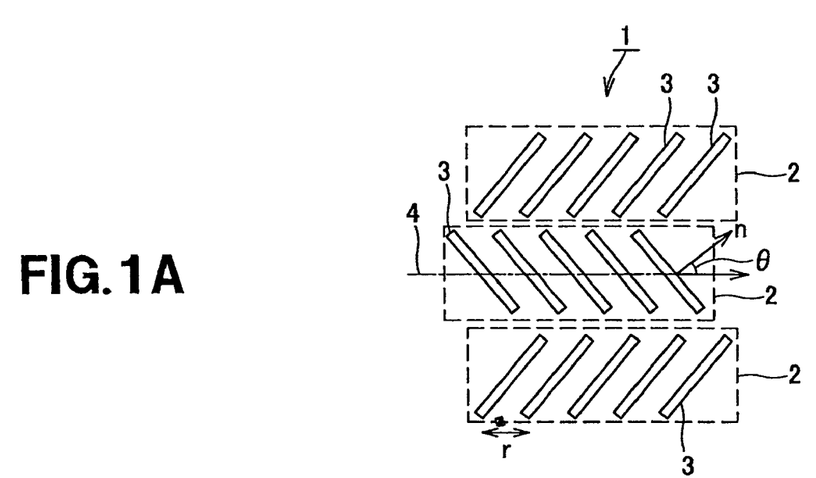

As shown in FIG. 1A, an organic single crystal 1 includes a plurality of columns 2. Each of the columns 2 has a structure that a plurality of planar organic compounds 3 are arranged so that molecular planes of molecules are respectively parallel to each other. Further, the columns 2 are respectively arranged so that the longitudinal direction of each of the columns 2 corresponds to the direction of a first crystallographic axis 4 (refer it also to as a stack axis, hereinafter).

The organic compounds 3 are arranged in the column 2 so that the an angle θ formed by the normal n of the molecular plane and the stack axis is larger than 0°. As examples of the organic compound 3, molecules having planar and wide molecular planes are exemplified which include phthalocyanines such as phthalocyanine as shown by a below-described chemical formula 1 or phthalocyanine complexes as shown in a chemical formula 2, and porphyrins such as tetrabenzoporphyrin as shown by a chemical formula 3 or tetrabenzoporphyrin complexes as shown by a chemical formula 4.

[Chemical Formula 5]

[Chemical Formula 6]

M represents bivalent metal ion.

[Chemical Formula 7]

[Chemical Formula 8]

M represents bivalent metal ion.

Further, the organic single crystal 1 has atoms arranged on the peripheral edges of each column 2. The atoms are thin in electron density and weak in interatomic force (not illustrated. Refer them to as peripheral atoms, hereinafter). Such peripheral atoms are arranged on the peripheral edges of the column 2 to weaken an interaction generated between the columns 2. In this embodiment, on the peripheral edge of each column 2, hydrogen atom is arranged.

Figure 1B:
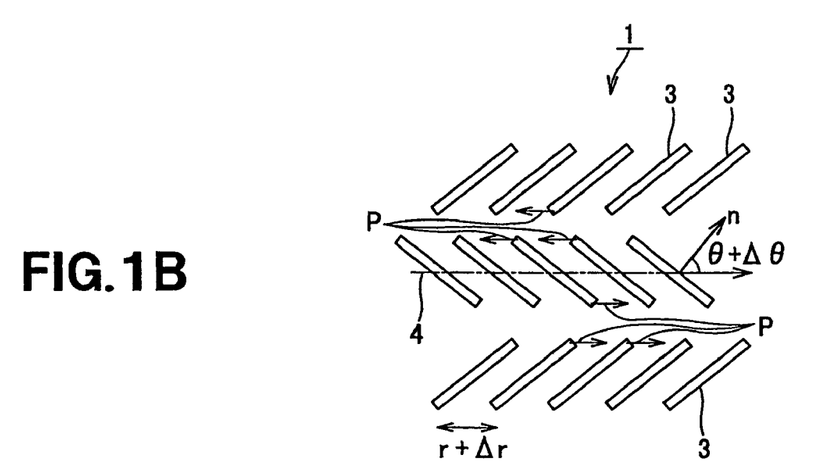

In the organic single crystal 1, when a force is exerted in the direction of the stack axis 4, as shown in FIG. 1B, the inclination of the organic compounds 3 forming the column 2 relative to the stack axis 4 changes. An angle θ formed by the normal n of the molecular plane of each of the organic compounds 3 and the stack axis 4 changes to θ+Δθ. θ is an angle larger than 0°. Further, as the angle θ formed by the normal n of the molecular plane of each of the organic compounds 3 and the stack axis 4 changes to θ+Δθ, a space r between the adjacent organic compounds 3 along the direction of the stack axis 4 (refer it also to as a lattice spacing, hereafter) changes to r+Δr.

When the force is exerted in the direction of the stack axis 4, the organic single crystal 1 changes as shown in FIG. 1B. Thus, the organic single crystal 1 has flexibility. Accordingly, the organic single crystal 1 can form a flexible electronic device deformed in accordance with an exerted force when the force is externally exerted. Further, when the organic single crystal 1 has an electric conductivity, the organic single crystal 1 can be also used as a material of a flexible electric conductor such as a material of the channel layer and the wiring electrode of a transistor.

When the force is exerted in the direction of the stack axis 4 so that the organic single crystal 1 changes as shown in FIG. 1B, the peripheral atoms disposed between the columns 2 weaken intermolecular force of the columns 2 to move in the same direction as the direction in which the organic compounds 3 are inclined as shown by arrow marks P. Thus, the peripheral atoms do not prevent the organic compounds 3 from being inclined.

Figure 2A:
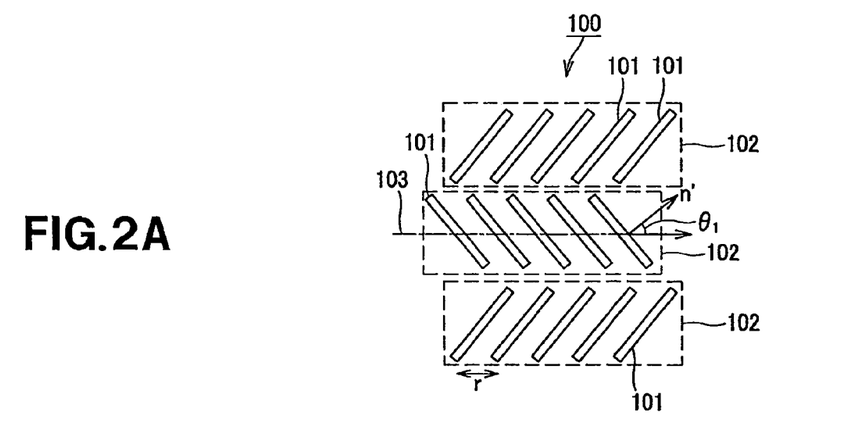
FIGS. 2A-2C are schematic views showing the organic single crystal having a plurality of columns in which a plurality of planar organic compounds is arranged so that the molecular planes of molecules are respectively parallel.
Figure 2B:
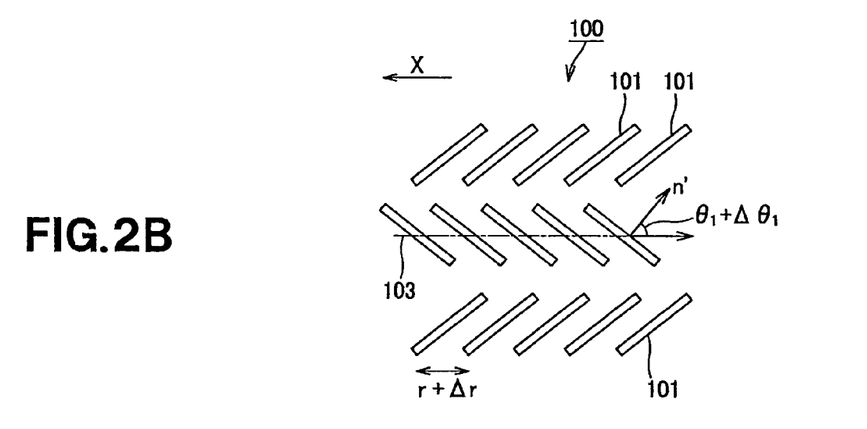

As shown in FIG. 2A, in an organic single crystal 100, a plurality of columns 102 are provided. In each of the columns 102, a plurality of planar organic compounds 101 are arranged so that molecular planes of molecules are respectively parallel to each other. The longitudinal direction of each of the columns 102 is arranged so as to correspond to the direction of a stack axis 103. The normal n' of the molecular plane of each of the organic compounds 101 is arrange at a prescribed angle relative to the stack axis 103. When a force along the direction of the stack axis 103 is exerted on the organic single crystal 100 as shown by an arrow mark X in FIG. 2, an angle $\theta_1$ formed by the normal n' of the molecular plane of each of the organic compounds 101 forming each column 102 and the stack axis 103 changes $\theta_1+\Delta\theta_1$, as Shown in FIG. 2B. Otherwise, as shown in FIG. 2C, the organic compounds 101 forming each of the columns 102 move in the direction of the stack axis 103 so that an angle $\theta_1$ formed by the normal n' of the molecular plane of each of the organic compounds 101 and the stack axis 103 remains to be constant.

Figure 2C:
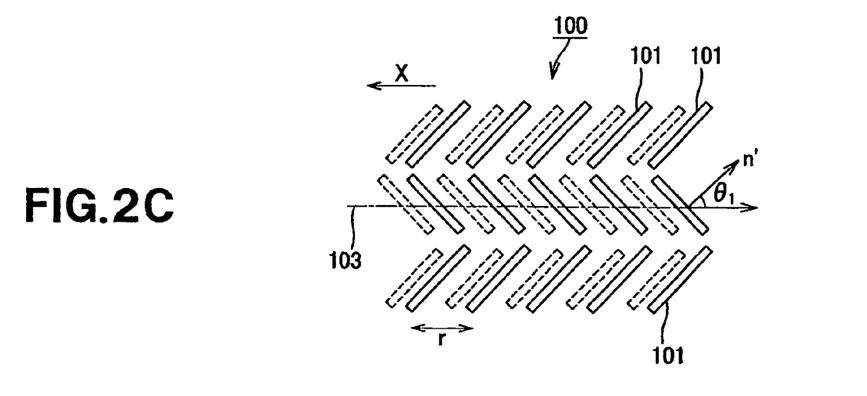

Dotted lines in FIG. 2C show the positions of the organic compounds 101 before the force shown by the arrow mark X is exerted on the organic single crystal 100. Solid lines show the positions of the organic compounds 101 after the force shown by the arrow mark X is exerted on the organic single crystal 100.

To provide the flexibility for the organic single crystal 100, when the force is exerted in the direction of the stack axis 103, the inclination of each of the organic compounds 101 forming each of the columns 102 relative to the stack axis 103 needs to change so that the angle $\theta_1$ formed by the normal n' of the molecular plane of each of the organic compounds 101 and the stack axis 103 changes to $\theta_1+\Delta\theta_1$, as shown in FIG. 2B. Now, conditions under which the change as shown in FIG. 2B is generated in the organic single crystal 100 will be described below.

The energy of the organic single crystal 100 per unit volume is modeled as shown by a following formula 1.

$$U(r) = -A\{1-(r^2-d^2)^{1/2}/L\} + \alpha V(s)$$ Formula 1

Figure 3:
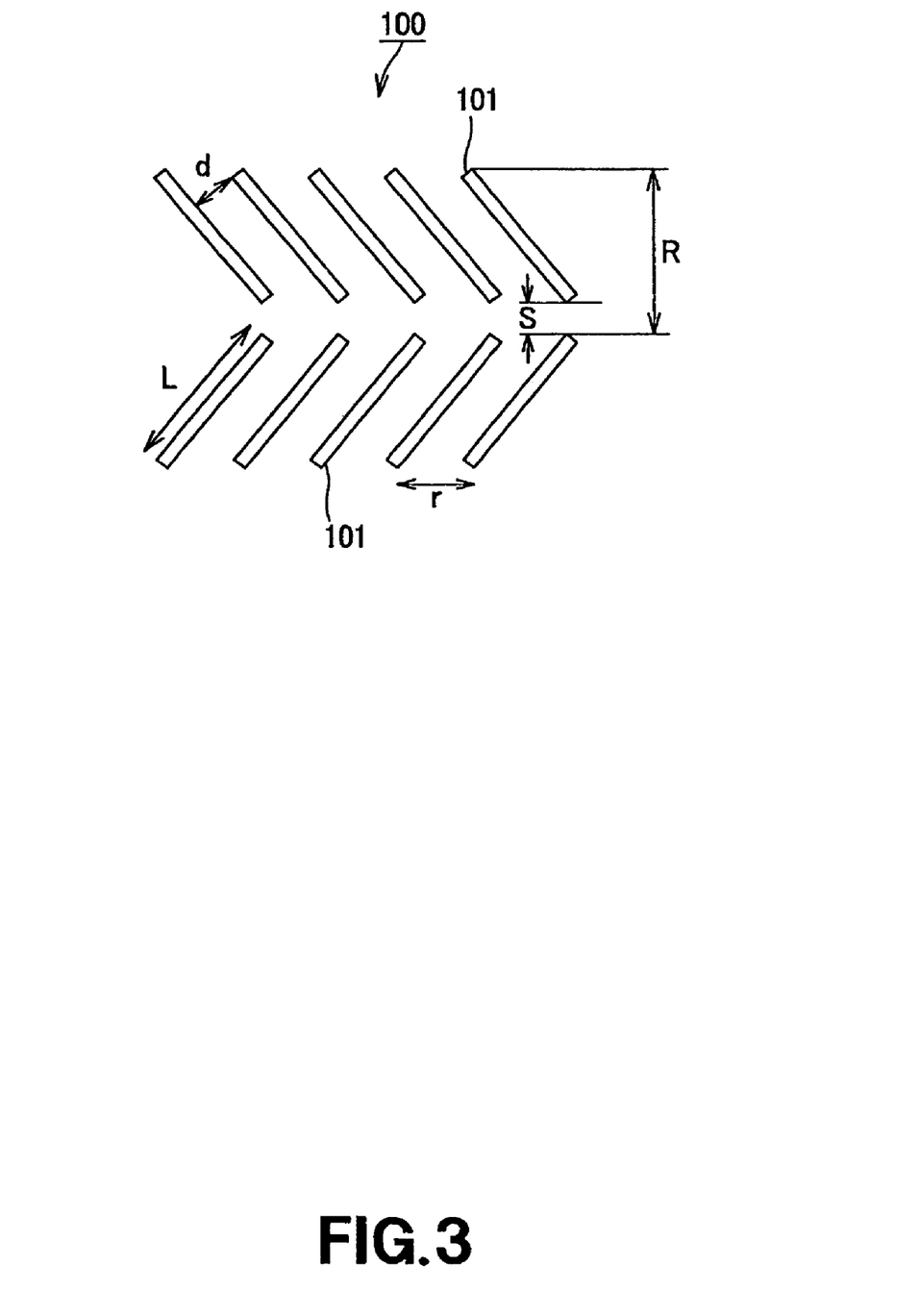
FIG. 3 is a view for explaining parameters used in a formula 1.

Here, as shown in FIG. 3, r designates a lattice spacing, d designates a distance between the mutually adjacent organic compounds 101 and L designates the length of each of the organic compounds 101 along the direction of an inclination of $\theta$ relative to the stack axis 103. Further, A represents energy when the mutually adjacent organic compounds 101 along the direction of the stack axis 103 are completely overlapped in an adjacent state a is a constant. Further, V(s) is a formula showing an interaction between the mutually adjacent columns 102 as shown by a following formula 2. s designates a distance between the mutually adjacent columns 102. R designates the width of the column 102 along the direction perpendicular to the stack axis 103. $\alpha$ and A are constants determined by the size of the organic compound 101 or the extent of the molecular plane.

$$V(s) = -\mu\{Ld(R-s)\}^6 + \nu/\{Ld(R-s)\}^{12}$$ Formula 2

Further, s and r have a relation shown by a following formula 3.

$$s = R - Ld/r$$ Formula 3

Figure 4:
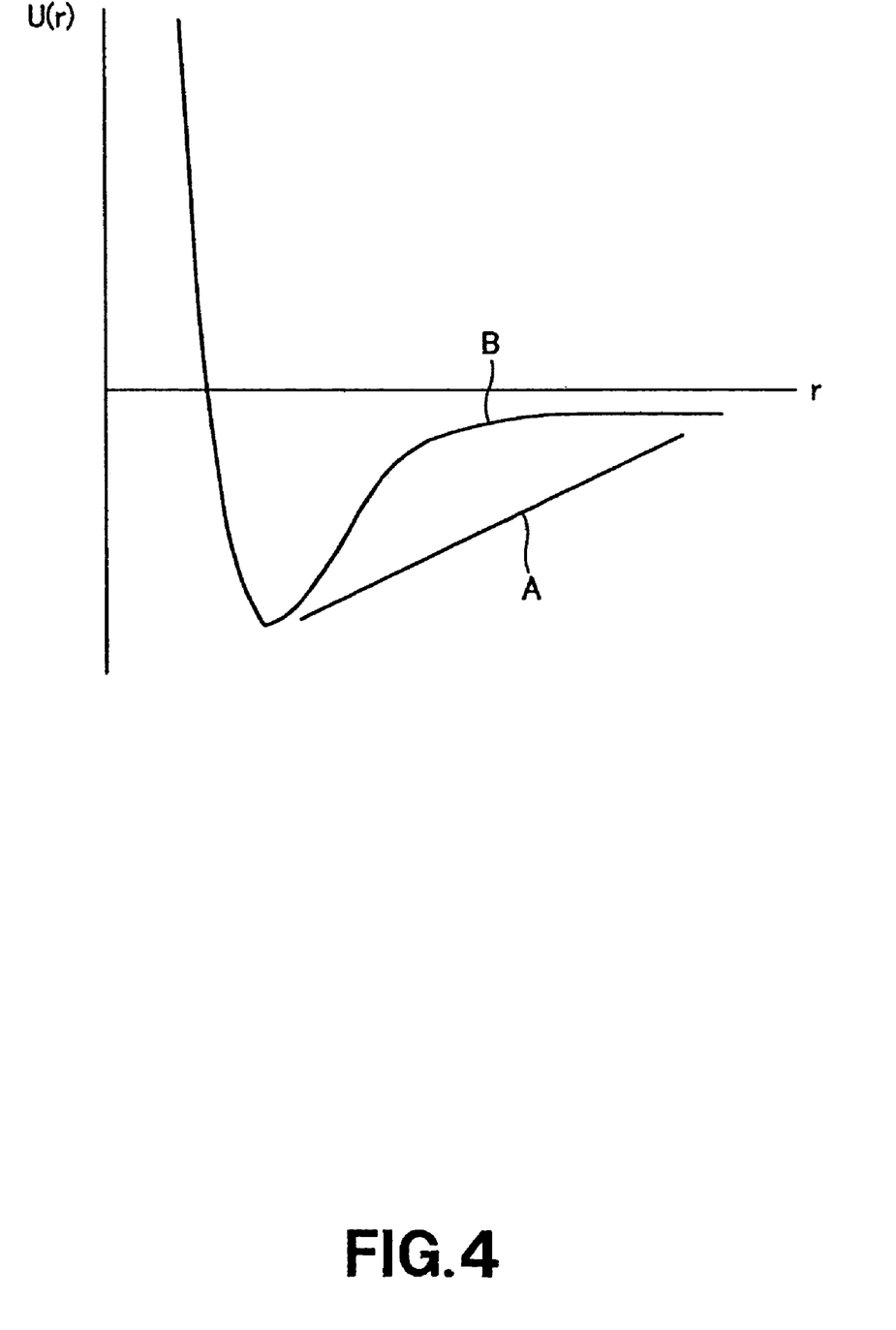
FIG. 4 is a diagram showing that the inclination of U(r) approximates to A/L.

A first item in the formula 1 indicates an interaction between the organic compounds 101 in the column 102 and a second item indicates an interaction between the columns 102. However, since the hydrogen atom is arranged in the peripheral edge of each of the columns 102, the second item does not have a substantial effect except a case that s is small, that is, r is small. Further, in the formula 1, as r increases, the first item becomes active. As shown by A in FIG. 4, it is recognized that U(r) approximates to Ar/L−A, namely, the inclination gradually comes near to A/L.

Further, an ordinary intermolecular interaction is shown by a following formula 4.

$$V(r) = -\mu/r^6 + \nu/r^{12}$$ Formula 4.

Here, $\mu$ and $\nu$ are constants. Further, the change of the intermolecular interaction shown in the formula 4 is represented by B in FIG. 4.

Since U(r) approximates to Ar/L−A, as L of the organic compounds 101 decreases, the energy represented by the formula 1 increases and exceeds the energy represented by the formula 4. That is, the ordinary intermolecular interaction shown by the formula 4 acts between the organic compounds 101 forming the organic single crystal 100.

Accordingly, in case L is smaller than a prescribed value, when the force along the direction of the stack axis 103 is exerted on the organic single crystal 100, the organic compounds 101 move in the direction along the stack axis 103 while the angle $\theta_1$ formed by the normal n' of the molecular plane of each of the organic compounds 101 and the stack axis 103 is maintained to be constant as shown in FIG. 2C. In this case, even when the force is exerted in the direction of the stack axis 103, the organic single crystal 100 does not exhibit such a change as shown in FIG. 2B and has no flexibility.

On the other hand, as the molecular plane of each of the organic compounds 101 becomes large and L becomes large, the energy represented by the formula 1 decreases and is lower than the energy represented by the formula 4. That is, the organic single crystal 100 has the energy shown by the formula 1.

Further, when the force is exerted in the direction of the stack axis 103 to have the change of the organic compounds 101 as shown in FIG. 2B, the change of energy of the organic single crystal 100 is proportional to the variation $\Delta r/r$ (refer it also to as a strain, hereinafter) of a space between the adjacent organic compounds 101. That is, to realize the flexibility of the organic compounds 101, it is required that there exists a range of strain over which the energy of the organic single crystal 100 changes in proportion to the strain.

As described above, in the organic single crystal 100 having the flexibility, L is not smaller than a prescribed value determined by the size or the form of the molecular plane of each of the organic compounds 101, the interaction between the organic compounds 101, etc. Further, there exists a range of strain over which the energy of the organic single crystal 100 changes in proportion to the strain.

Figure 5A:
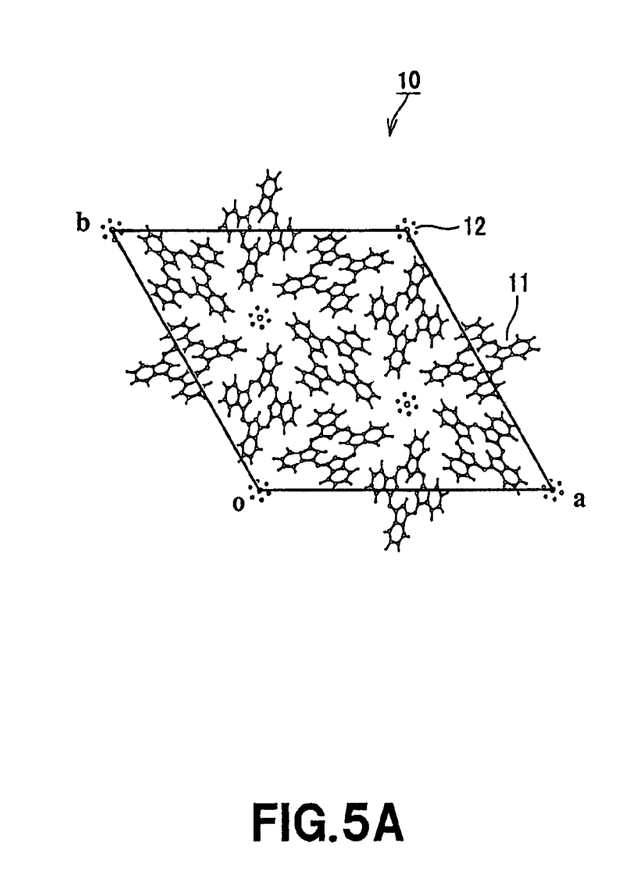
FIGS. 5A and 5B are schematic views showing $H_2PcTri$.
Figure 5B:
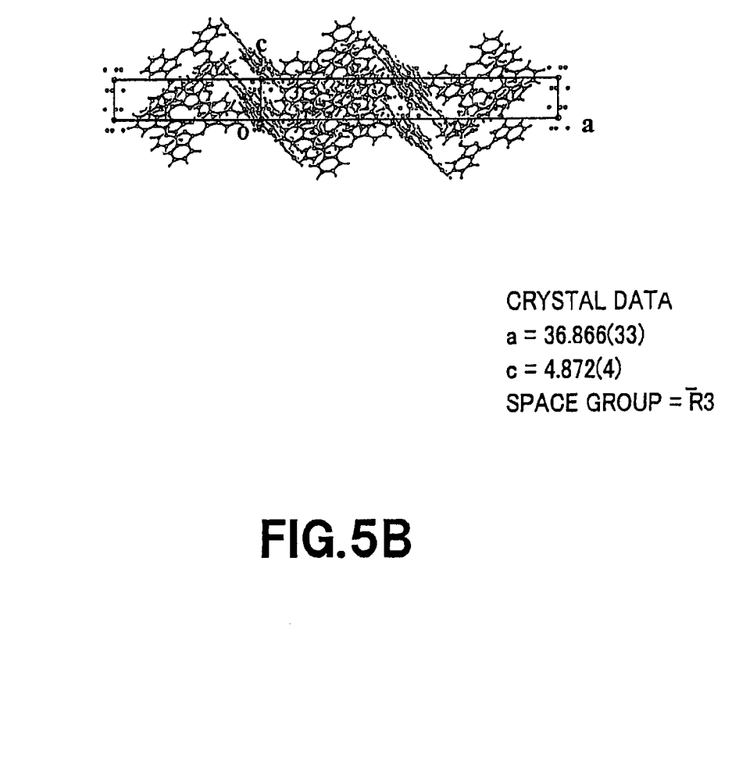

Now, a specific example of the organic single crystal 100 will be described below. As the specific example of the organic single crystal 100, for example, a single crystal $H_2Pc$ $(PCl_{0.53}F_{1.37}O_{4.10})_{0.298}$ (trigonal type) (refer it to as $H_2PcTri$, hereinafter) 10 including phthalocyanine shown by the chemical formula 1 as shown in FIGS. 5A and 5B may be exemplified.

In $H_2PcTri$ 10, it is recognized that a loop is wound by a single crystal of 30 μm×30 μm×2 cm. As shown in FIG. 5A, in $H_2PcTri$ 10, phthalocyanine 11 and $PCl_{0.53}F_{1.37}O_{4.10}$ 12 are regularly arranged along a plane formed by an axis a shown by a straight line oa and an axis b shown by a straight line ob in FIG. 5A. In $H_2PcTri$ 10, the ratio of phthalocyanine 11 to $PCl_{0.53}F_{1.37}O_{4.10}$ 12 is set to 1:0.298.

The crystal data of $H_2PcTri$ 10 is shown in a below described Table 1.

TABLE 1

| | |
|---|---|
| a | 36.866 (Deviation 33) |
| c | 4.872 (Deviation 4) |
| Space group | R3 |

Further, in $H_2PcTri$ 10, phthalocyanine 11 and $PCl_{0.53}F_{1.37}O_{4.10}$ 12 regularly arranged along the plane formed by the axis a and the axis b are stacked in the direction of a stack axis shown by a straight line oc (axis c) as shown in FIG. 5B.

Further, a column is formed by phthalocyanine 11 arranged in one row along the direction of the stack axis.

Figure 6:
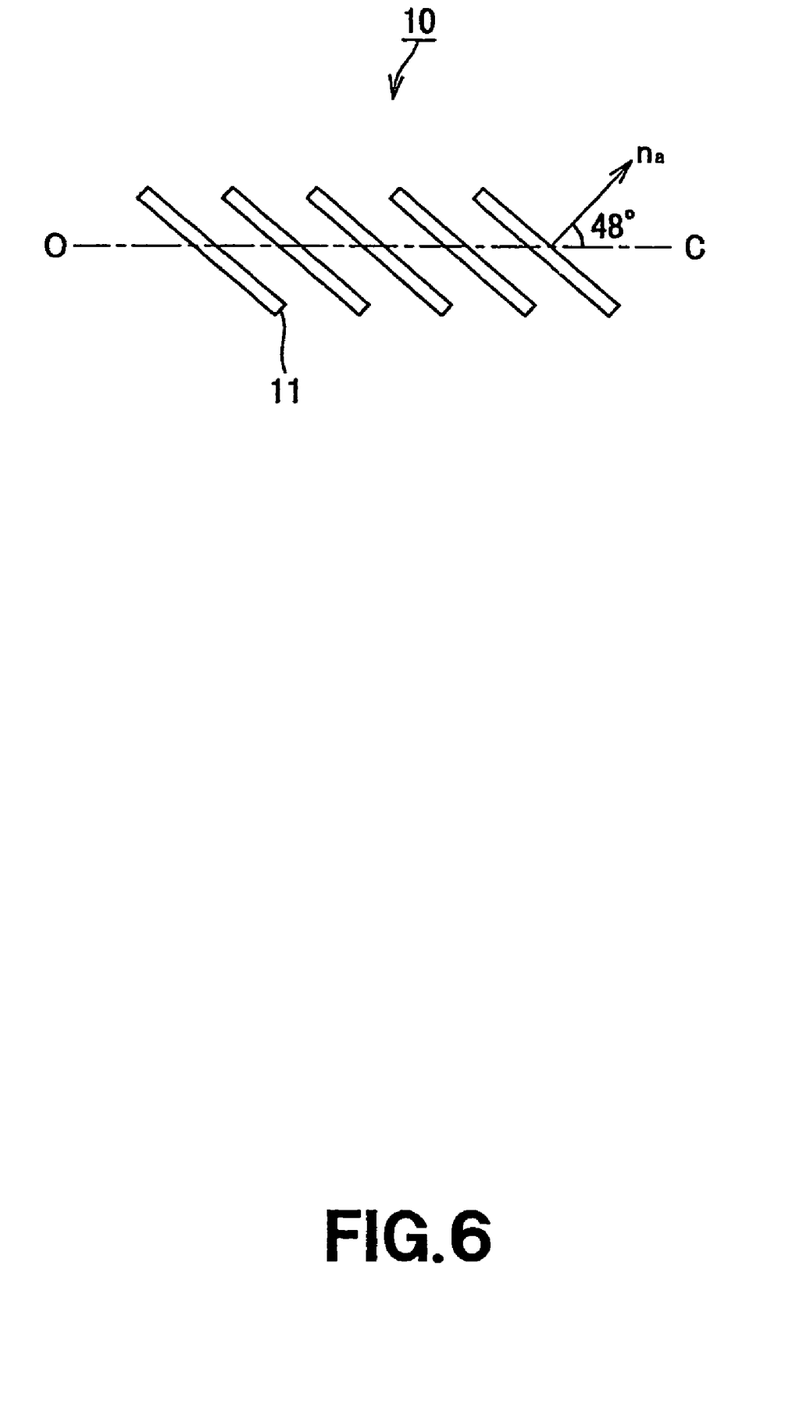
FIG. 6 is a diagram showing that phthalocyanine in $H_2PcTri$ is arranged at an angle of 48° relative to a stack axis.

Further, in $H_2PcTri$ 10, the peripheral edge of the column is covered with hydrogen atoms. Further, as shown in FIG. 6, in phthalocyanine 11 forming $H_2PcTri$ 10, the normal $n_a$ of a molecular plane is arranged at an angle of 48° relative to the stack axis. Further, in phthalocyanine 11 forming $H_2PcTri$ 10, since L is set to about 15 angstroms, the molecular plane is large, an overlapping area between molecules adjacent in the direction of the stack axis is large, and the energy represented by the formula 1 is lower than the energy represented by the formula 4.

Figure 7:
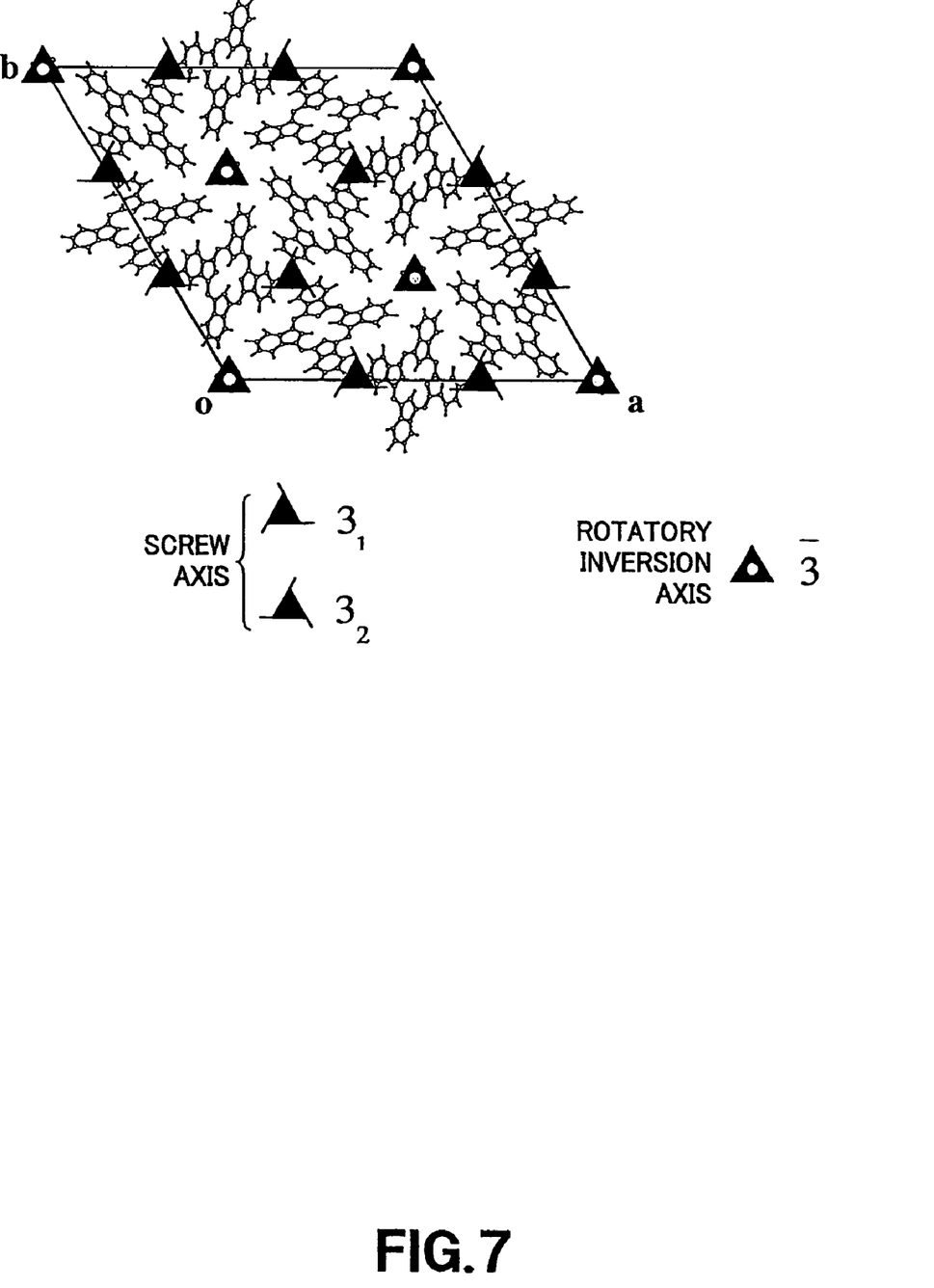
FIG. 7 is a diagram showing the arrangement of rotatory inversion axes and screw axes in $H_2PcTri$.

Further, in $H_2PcTri$ 10, as shown in FIG. 7, a rotatory inversion axis, a screw axis $3_1$ and a screw axis $3_2$ are alternately arrange along the direction of the axis a and the direction of the axis b.

Figure 8:
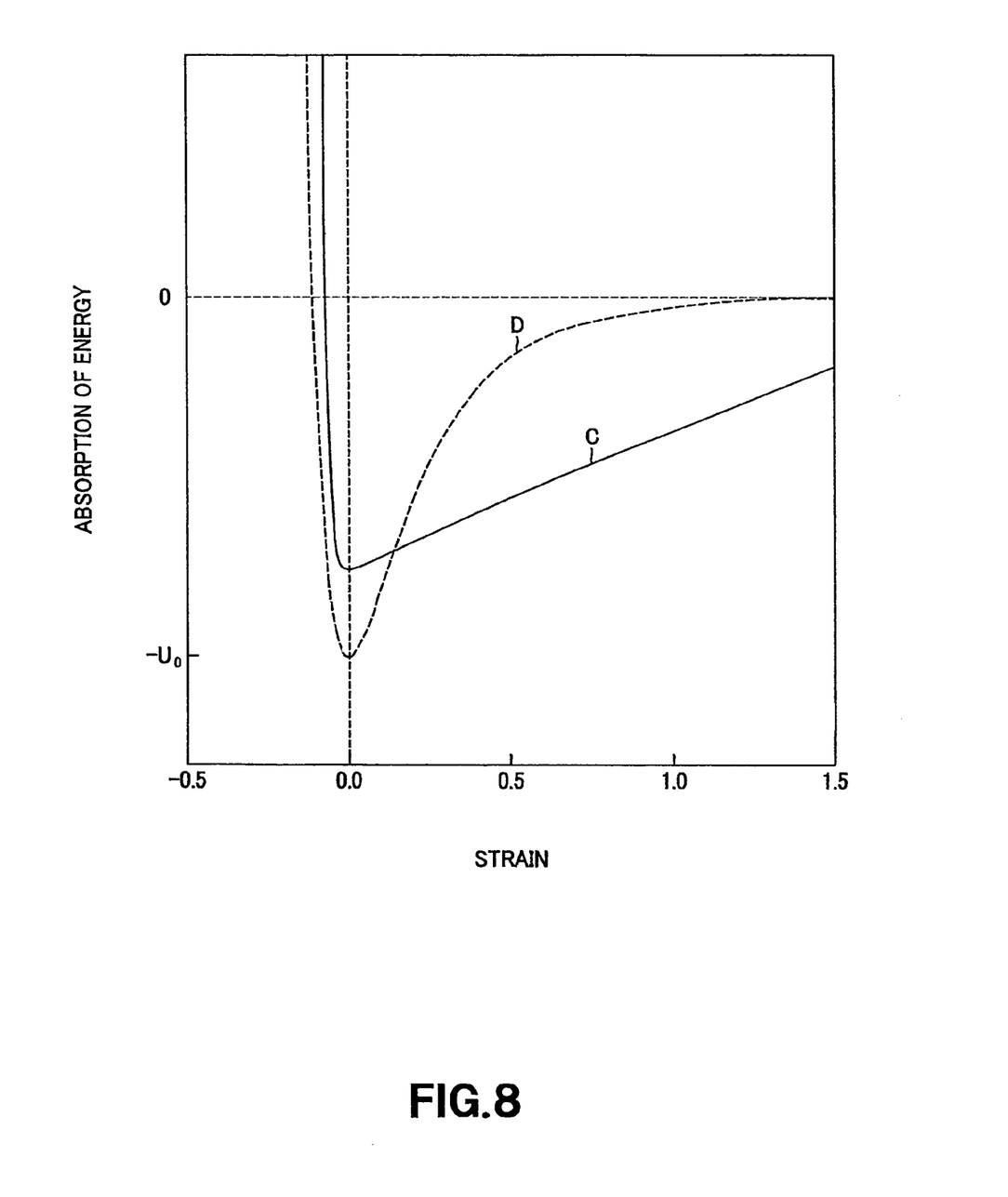
FIG. 8 is a diagram showing the change of energy per unit volume relative to a strain.

The change of the energy per unit volume corresponding to the strain for $H_2PcTri$ 10 is shown by C in FIG. 8. The change of the energy per unit volume gradually approximates to the strain so as to be proportional thereto.

Accordingly, $H_2PcTri$ 10 has the flexibility and is deformed in accordance with exerted force when the force along the direction of the stack axis is exerted thereon.

Further, $H_2PcTri$ 10 has an electric conductivity. Thus, $H_2PcTri$ 10 can be used as a wiring material and can be employed as a wiring material of a flexible electronic device or as a channel material of a transistor. Since $H_2PcTri$ 10 is a single crystal, $H_2PcTri$ 10 has no crystal interface. Thus, $H_2PcTri$ 10 is used as the channel material of the transistor, so that the diffusion of a carrier can be prevented. Accordingly, the flexible transistor high in its mobility of the carrier can be realized.

Figure 9A:
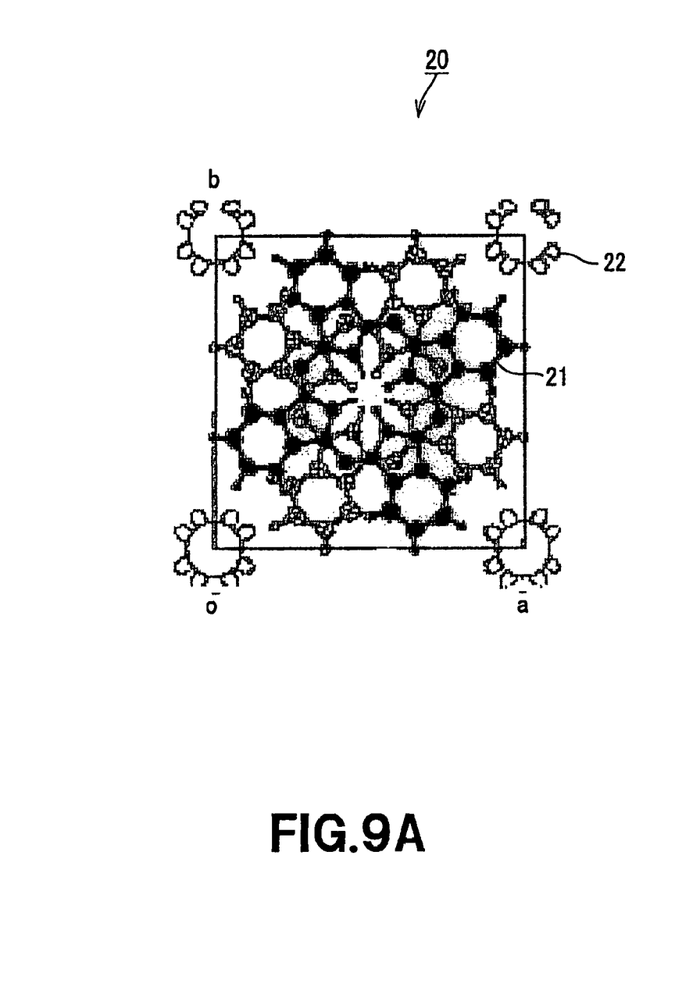
FIGS. 9A and 9B are schematic views showing $H_2PcTet$.
Figure 9B:
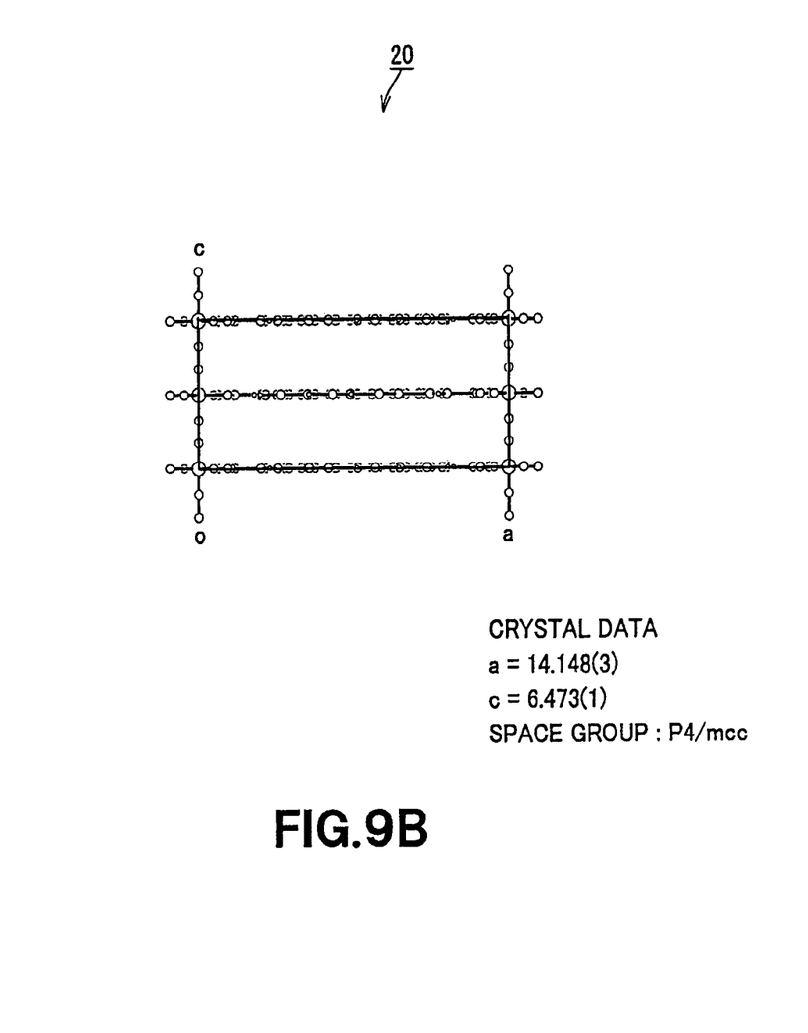

On the other hand, as the organic single crystal having no flexibility, $H_2Pc(PF_6)_{0.43}$ (tetragonal type) (refer it to as $H_2PcTet$, hereinafter) 20 as shown in FIGS. 9A and 9B may be exemplified.

In $H_2PcTet$ 20, phthalocyanine 11 and $PF_6$ 21 are regularly arranged along a plane formed by an axis a shown by a straight line oa and an axis b shown by a straight line ob in FIG. 9A. In $H_2PcTet$ 20, the ratio of phthalocyanine 11 to $PF_6$ 21 is set to 1:0.43.

The crystal data of $H_2PcTet$ 20 is shown in a below described Table 2.

TABLE 2

| | |
|---|---|
| a | 14.148 (Deviation 3) |
| c | 6.473 (Deviation 1) |
| Space group | P4/mcc |

Further, in $H_2PcTet$ 20, phthalocyanine 11 and $PF_6$ 21 regularly arranged along the plane formed by the axis a and the axis b are stacked in the direction of a stack axis shown by a straight line oc (axis c) as shown in FIG. 9B. Further, a column is formed by phthalocyanine 11 arranged in one row along the direction of the stack axis.

Further, in phthalocyanine 11 forming $H_2PcTet$ 20, since L is set to about 15 angstroms, the molecular plane is large, and the energy represented by the formula 1 is lower than the energy represented by the formula 4.

Figure 10:
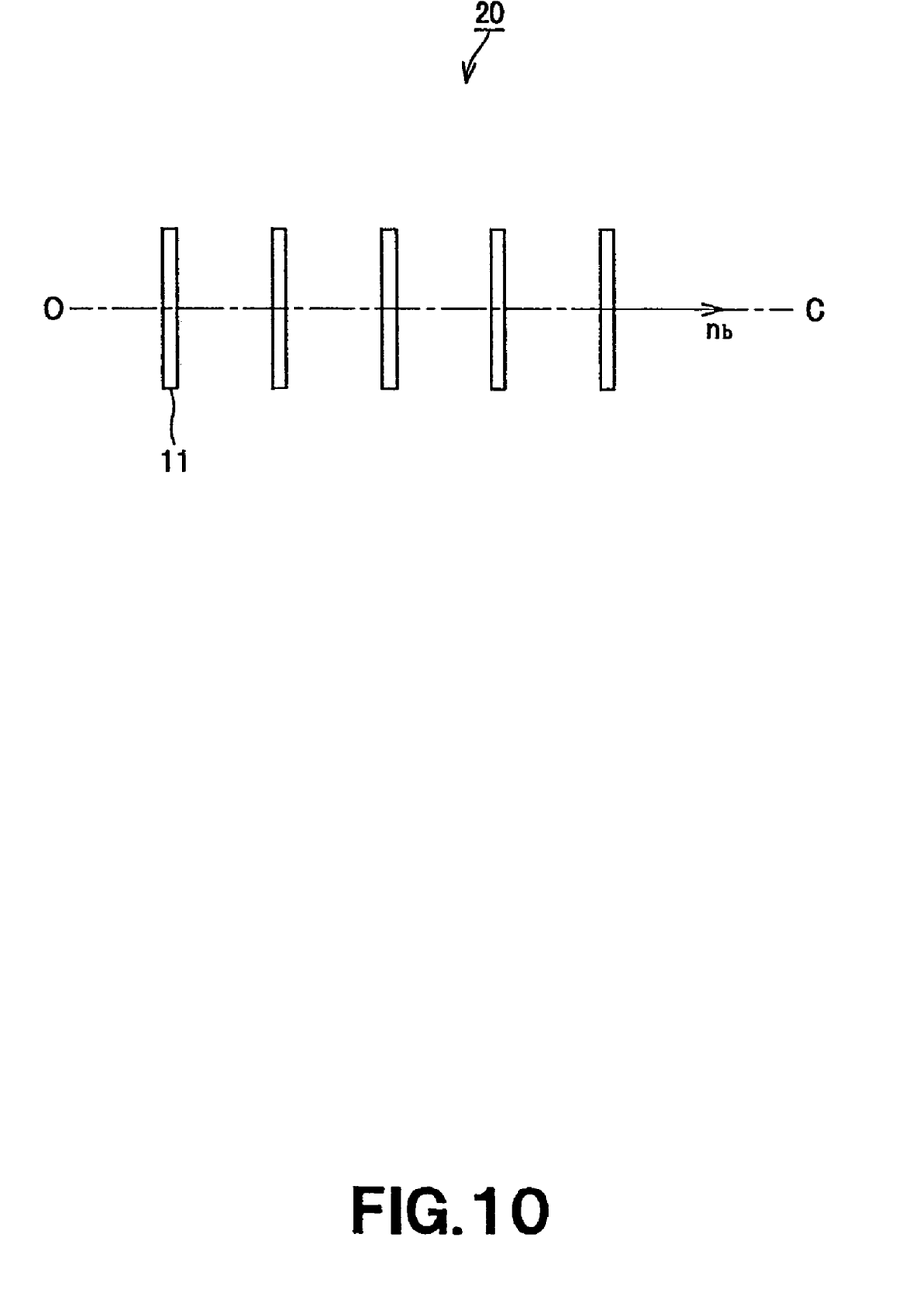
FIG. 10 is a diagram showing that phthalocyanine in $H_2PcTet$ is arranged at an angle of 90° relative to a stack axis.

However, in $H_2PcTet$ 20, the peripheral edge of the column is covered with hydrogen atoms. Further, as shown in FIG. 10, in phthalocyanine 11 forming $H_2PcTet$ 20, the stack axis is overlapped on the normal $n_b$ of each of the molecular planes of phthalocyanine 11. That is, an angle formed by the stack axis and the normal $n_b$ of the molecular plane of phthalocyanine 11 is 0°.

Further, the change of the energy per unit volume corresponding to the strain for $H_2PcTet$ 20 is shown by D in FIG. 8. The change of the energy per unit volume is not proportional to the change of a space between the adjacent phthalocyanine 11 and increases in a quadratic curve.

Therefore, $H_2PcTet$ 20 does not have flexibility and is not deformed in accordance with exerted force to be broken even when the force is externally exerted thereon.

Now, a method for producing $H_2PcTri$ 10 will be described below.

Figure 11:
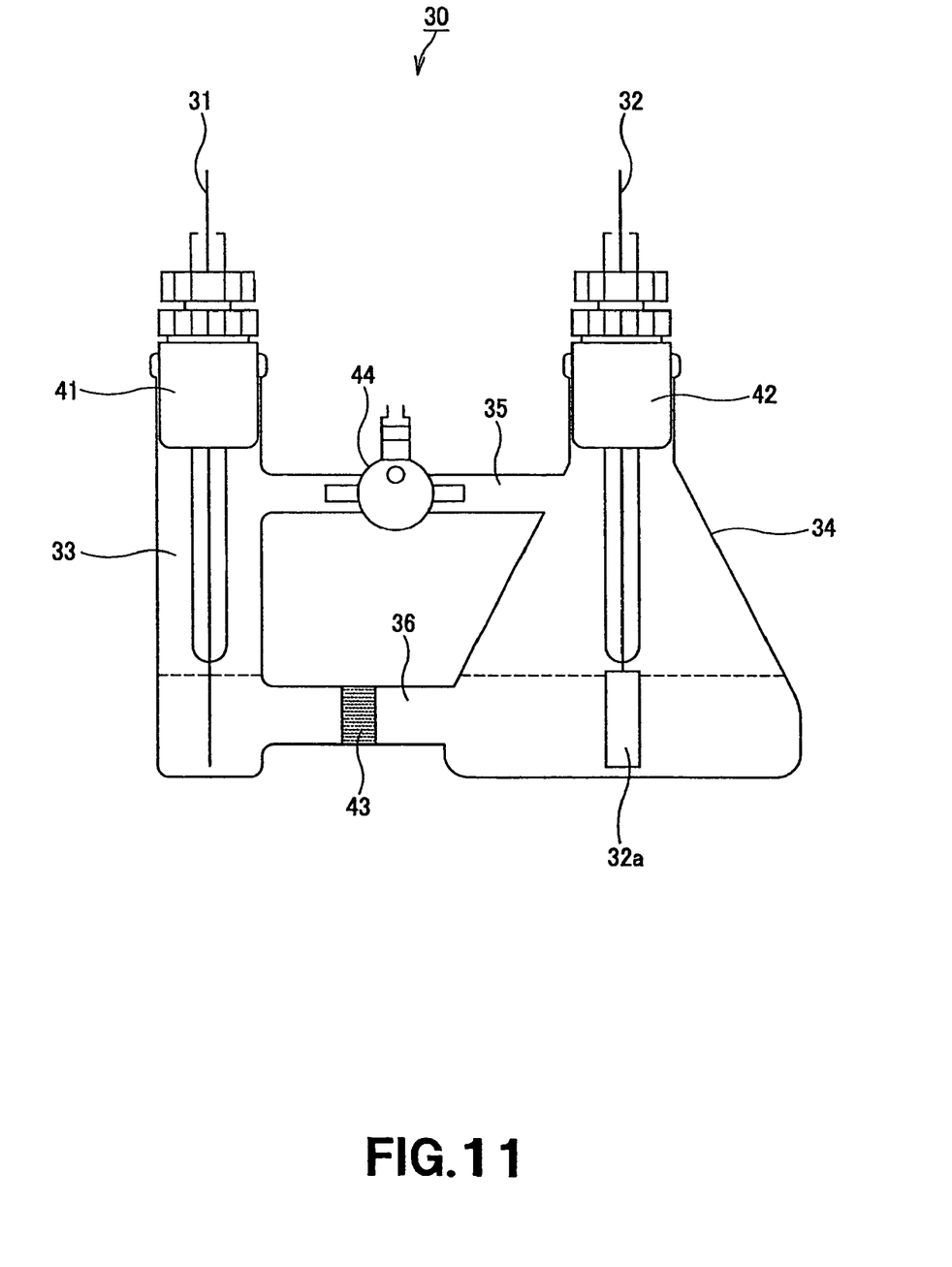
FIG. 11 is a schematic view showing a cell used for producing $H_2PcTri$.

$H_2PcTri$ 10 is produced by using a cell 30 shown in FIG. 11. The cell 30 includes a first electrode 31 serving as a cathode and a second electrode 32 serving as an anode. Further, the cell 30 has a structure that a first vessel 33 on which the first electrode 31 is mounted is connected to a second vessel 34 on which the second electrode 32 is mounted by a first connecting pipe 35 and a second connecting pipe 36.

The first electrode 31 is formed with platinum. The first electrode 31 is formed in an elongated and linear configuration and mounted on the first vessel 33 so as to pass through a below-described first Teflon plug 41.

The second electrode 32 is also formed with platinum. The second electrode 32 is formed in an elongated and linear configuration and has a platinum plate 32a mounted on one end part. The second electrode 32 is mounted on the second vessel 34 so as to pass through a below-described second Teflon plug 42. In other words, the second electrode 32 is mounted on the second vessel 34 so that the platinum plate 32a is located in the second vessel 34 and the other end part protrudes outside the second vessel 34.

The first vessel 33 and the second vessel 34 have upper surfaces opened and the first Teflon plug 4 and the second Teflon plug 42 are respectively inserted into the vessels 33 and 34. The first vessel 33 is sealed to the first Teflon plug 41, and the second vessel 34 is sealed to the second Teflon plug 42 respectively by an interchangeable ground joint.

Further, the first Teflon plug 41 is sealed to the first electrode 31, and the second Teflon plug 42 is sealed to the second electrode 32 respectively by O-ring seals.

The first connecting pipe 35 and the second connecting pipe 36 are substantially horizontally provided. The first connecting pipe 35 is provided in the opening side of the first vessel 33 and the second vessel 34 and the second connecting pipe 36 is provided in the bottom surface side of the first vessel 33 and the second vessel 34. The inner part of the first vessel 33 is connected to the inner part of the second vessel 34 through the first connecting pipe 35 and the second connecting pipe 36. The second connecting pipe 36 is provided with a glass filter 43. In the first connecting pipe 35, a three-way cock 44 connected to an external device which is not shown is provided.

The above-described cell 30 is filled with phthalocyanine of 120 mg and 1-chloronaphthalene of 50 ml, and phthalocyanine is heated and dissolved at 140° C. under an atmosphere of argon as much as possible. Then, after lowering temperature to 120° C., TBA (tetrabutyl ammonium).$PF_6$ of 300 mg is added and dissolved. The temperature is maintained at constant 120° C., and the constant current of 0.5 to 8 μA is supplied between the first electrode 31 and the second electrode 32 for one week. Thus, a large quantity of $H_2PcTri$ precipitates in the anode side, that is, in the second electrode 32.

As described above, the organic single crystal 1 has a plurality of columns 2. The column 2 has a structure that the plurality of planar organic compounds 3 are arranged so that the molecular planes of molecules are respectively parallel to each other. Each of the columns 2 is arranged so that the longitudinal direction corresponds to the direction of the stack axis 4. In the organic single crystal 1, L is not smaller than a prescribed value. Further, there exists a range of strain over which the energy of the organic single crystal 1 changes in proportion to the strain.

Accordingly, the organic single crystal 1 to which the present invention is applied is a single crystal in which the organic compounds 3 are regularly arranged. However, when the force in the direction of the stack axis 4 is exerted on the organic single crystal, the organic single crystal has the flexibility that the inclination of each of the organic compounds 3 forming the column 2 relative to the stack axis 4 changes so that the angle θ formed by the normal n of the molecular plane of each of the organic compounds 3 and the stack axis 4 changes to θ+Δθ as shown in FIG. 1B.

Further, since the organic single crystal 1 to which the present invention is applied is the single crystal, the organic single crystal has no crystal interface. Accordingly, when the organic single crystal 1 has an electric conductivity, the organic single crystal 1 is used as the channel material of the transistor so that the diffusion of the carrier is not generated on the crystal interface. Accordingly, the flexible transistor having the high mobility of the carrier can be realized.

The present invention is not limited to the single crystal. For instance, an organic crystal having the structure described in this embodiment or the change of energy, which is not a single crystal, may have flexibility.

While the invention has been described in accordance with certain preferred embodiment thereof illustrated in the accompanying drawings and described in the above description in detail, it should be understood by those ordinarily skilled in the art that the invention is not limited to the embodiments, but various modifications, alternative constructions or equivalents can be implemented without departing from the scope and spirit of the present invention as set forth and defined by the appended claims.

What is claimed is:

1. An organic crystal having a plurality of columns, the plurality of columns including a plurality of planar organic compounds arranged so that molecular planes are respectively parallel to each other, a major axis of each of the columns being arranged along the direction of a first crystallographic axis, wherein an interaction generated between the adjacent planar organic compounds in the column is stronger than an interaction between the columns, and when a force along the direction of the first crystallographic axis is exerted, an angle formed by a normal of the molecular plane of each organic compound and the first crystallographic axis is equally changed in accordance with the exerted force; wherein the organic compounds are organic compounds represented by following chemical formula 1, chemical formula 2, chemical formula 3, or chemical formula 4,

[Chemical Formula 1]

[Chemical Formula 2]

M represents bivalent metal ion

[Chemical Formula 3]

[Chemical Formula 4]

M represents bivalent metal ion.

* * * * *